United States Patent
Jiang et al.

(10) Patent No.: US 11,629,180 B2
(45) Date of Patent: Apr. 18, 2023

(54) BIFUNCTIONAL ANGIOGENESIS INHIBITOR AND USE THEREOF

(71) Applicant: Remegen Co., Ltd., Shandong (CN)

(72) Inventors: Jing Jiang, Shandong (CN); Jianmin Fang, Shandong (CN); Xuejing Luan, Shandong (CN); Xuejing Yao, Shandong (CN); Ling Wang, Shandong (CN)

(73) Assignee: Remegen Co., Ltd., Shandong (CN)

( * ) Notice: Subject to any disclaimer, the term of this patent is extended or adjusted under 35 U.S.C. 154(b) by 219 days.

(21) Appl. No.: 16/981,652

(22) PCT Filed: Dec. 4, 2019

(86) PCT No.: PCT/CN2019/122854
§ 371 (c)(1),
(2) Date: Sep. 16, 2020

(87) PCT Pub. No.: WO2020/114411
PCT Pub. Date: Jun. 11, 2020

(65) Prior Publication Data
US 2021/0324039 A1 Oct. 21, 2021

(30) Foreign Application Priority Data
Dec. 7, 2018 (CN) .......................... 201811491023.1

(51) Int. Cl.
*C07K 14/71* (2006.01)
*A61K 38/00* (2006.01)

(52) U.S. Cl.
CPC .............. *C07K 14/71* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 2008/0171689 | A1 | 7/2008 | Williams et al. |
| 2009/0264358 | A1 | 10/2009 | Yu |
| 2010/0087627 | A1 | 4/2010 | Marshall et al. |
| 2013/0190235 | A1 | 7/2013 | Fang et al. |

FOREIGN PATENT DOCUMENTS

| CN | 1915427 A | 2/2007 |
| CN | 102219859 A | 10/2011 |
| JP | 2011529705 A | 12/2011 |
| JP | 2014513940 A | 6/2014 |
| JP | 2014519308 A | 8/2014 |
| RU | 2560589 C2 | 8/2015 |
| WO | WO 2007/014123 A2 | 2/2007 |
| WO | WO 2012/159548 A1 | 11/2012 |
| WO | WO 2021/004549 A1 | 1/2021 |

OTHER PUBLICATIONS

Jafarlou et al., Journal of Biological Regulators & Homeostatic Agents, 2016: 30: 315-321 (Year: 2016).*
Chiu et al., Int. J. Mol. Sci. 2021, 22, 4534 (Year: 2021).*
Nagy et al., Cells 2019, 8, 999; doi:10.3390/cells8090999 (Year: 2019).*
Mellado et al., Front. Immunol. 6:384. doi: 10.3389/fimmu.2015.00384 (Year: 2015).*
Denise K. Marciano, Pediatr Nephrol (2017) 32:7-20 (Year: 2017).*
Jiang et al., European Journal of Pharmaceutical Sciences vol. 121, Aug. 30, 2018: 251-259 (Year: 2018).*
Russian Office Action in Russian Application No. 2020131764 dated Jun. 24, 2021.
Shchuko, A.G., et al., "Angiogenesis inhibitors in treatment of different types of vascular and neovascular ocular pathology," Ophthalmosurgery, No. 2, pp. 30-35 (2012).
European Search Report in European Patent Application No. 19892434.2 dated Mar. 17, 2022.
Japanese First Office Action in Japanese Patent Application No. 2021-534423 dated Mar. 1, 2022.
English Translation of International Search Report, PCT/CN2019/122854, dated Mar. 9, 2020.
Chen, C-H. et al. 2004 "Fibroblast Growth Factor 2: From Laboratory Evidence to Clinical Application" Current Vascular Pharmacology, 2, 33-43.
Cross, M.J. et al. 2002 "FGF and VEGF function in angiogenesis: signalling pathways, biological responses and therapeutic inhibition" TRENDS in Pharmacological Sciences vol. 22 No. 4: 201-207.
Hagedorn, Mand Bikfalvi, A. 2000 "Target molecules for antiangiogenic therapy: from basic research to clinical trials" Critical Reviews in Oncology:Hematology 34 (2000) 89-110.
Ozaki, H. et al. 2003 "Effects of endostatin in proliferative diabetic retinopathy" J. Tokyo Med. Univ 61(3) 226-231.
Simons, M. 2005 "Angiogenesis, Arteriogenesis, and Diabetes. Paradigm Reassessed?" Journal of the American College of Cardiology vol. 46, No. 5: 835-837.
Stratman, A.N. et al. 2022 "VEGF and FGF prime vascular tube morphogenesis and sprouting directed by hematopoietic stem cell cytokines", Blood. 2011;117(14):3709-3719).
Suganthalakshmi, B. et al. 2006 "Association of VEGF and eNOS gene polymorphisms in type 2 diabetic retinopathy" Molecular Vision 2006; 12:336-41.

* cited by examiner

*Primary Examiner* — Christina M Borgeest
(74) *Attorney, Agent, or Firm* — Knobbe, Martens, Olson & Bear, LLP

(57) ABSTRACT

The present invention relates to a bifunctional angiogenesis inhibitor, which has VEGF inhibitory activity and FGF inhibitory activity, and can inhibit VEGF and FGF dual factors-induced or high glucose-induced cell proliferation, cell migration, and/or lumen formation. The present invention also relates to the use of the bifunctional angiogenesis inhibitor in inhibiting retinal angiogenesis, such as diabetic retinopathy, age-related macular degeneration and the like.

21 Claims, 1 Drawing Sheet
Specification includes a Sequence Listing.

SEQUENCE LISTING

```
<160> NUMBER OF SEQ ID NOS: 3

<210> SEQ ID NO 1
<211> LENGTH: 641
<212> TYPE: PRT
<213> ORGANISM: Artificial Sequence
<220> FEATURE:
<223> OTHER INFORMATION: Fusion Protein

<400> SEQUENCE: 1

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125
```

-continued

```
Val Gly Ile Asp Phe Asn Trp Glu Tyr Pro Ser Ser Lys His Gln His
    130                 135                 140
Lys Lys Leu Val Asn Arg Asp Leu Lys Thr Gln Ser Gly Ser Glu Met
145                 150                 155                 160
Lys Lys Phe Leu Ser Thr Leu Thr Ile Asp Gly Val Thr Arg Ser Asp
                165                 170                 175
Gln Gly Leu Tyr Thr Cys Ala Ala Ser Ser Gly Leu Met Thr Lys Lys
            180                 185                 190
Asn Ser Thr Phe Val Arg Val His Glu Lys Pro Val Ala Pro Tyr Trp
        195                 200                 205
Thr Ser Pro Glu Lys Met Glu Lys Lys Leu His Ala Val Pro Ala Ala
210                 215                 220
Lys Thr Val Lys Phe Lys Cys Pro Ser Ser Gly Thr Pro Asn Pro Thr
225                 230                 235                 240
Leu Arg Trp Leu Lys Asn Gly Lys Glu Phe Lys Pro Asp His Arg Ile
                245                 250                 255
Gly Gly Tyr Lys Val Arg Tyr Ala Thr Trp Ser Ile Ile Met Asp Ser
            260                 265                 270
Val Val Pro Ser Asp Lys Gly Asn Tyr Thr Cys Ile Val Glu Asn Glu
        275                 280                 285
Tyr Gly Ser Ile Asn His Thr Tyr Gln Leu Asp Val Val Glu Arg Ser
    290                 295                 300
Pro His Arg Pro Ile Leu Gln Ala Gly Leu Pro Ala Asn Lys Thr Val
305                 310                 315                 320
Ala Leu Gly Ser Asn Val Glu Phe Met Cys Lys Val Tyr Ser Asp Pro
                325                 330                 335
Gln Pro His Ile Gln Trp Leu Lys His Ile Glu Val Asn Gly Ser Lys
            340                 345                 350
Ile Gly Pro Asp Asn Leu Pro Tyr Val Gln Ile Leu Lys Thr Ala Gly
        355                 360                 365
Val Asn Thr Thr Asp Lys Glu Met Glu Val Leu His Leu Arg Asn Val
    370                 375                 380
Ser Phe Glu Asp Ala Gly Glu Tyr Thr Cys Leu Ala Gly Asn Ser Ile
385                 390                 395                 400
Gly Leu Ser His His Ser Ala Trp Leu Thr Val Leu Glu Ala Asp Lys
                405                 410                 415
Thr His Thr Cys Pro Pro Cys Pro Ala Pro Glu Leu Leu Gly Gly Pro
            420                 425                 430
Ser Val Phe Leu Phe Pro Pro Lys Pro Lys Asp Thr Leu Met Ile Ser
        435                 440                 445
Arg Thr Pro Glu Val Thr Cys Val Val Val Asp Val Ser His Glu Asp
    450                 455                 460
Pro Glu Val Lys Phe Asn Trp Tyr Val Asp Gly Val Glu Val His Asn
465                 470                 475                 480
Ala Lys Thr Lys Pro Arg Glu Glu Gln Tyr Asn Ser Thr Tyr Arg Val
                485                 490                 495
Val Ser Val Leu Thr Val Leu His Gln Asp Trp Leu Asn Gly Lys Glu
            500                 505                 510
Tyr Lys Cys Lys Val Ser Asn Lys Ala Leu Pro Ala Pro Ile Glu Lys
        515                 520                 525
Thr Ile Ser Lys Ala Lys Gly Gln Pro Arg Glu Pro Gln Val Tyr Thr
    530                 535                 540
```

```
Leu Pro Pro Ser Arg Asp Glu Leu Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Lys Leu Thr Val Asp Lys
            595                 600                 605

Ser Arg Trp Gln Gln Gly Asn Val Phe Ser Cys Ser Val Met His Glu
        610                 615                 620

Ala Leu His Asn His Tyr Thr Gln Lys Ser Leu Ser Leu Ser Pro Gly
625                 630                 635                 640

Lys

<210> SEQ ID NO 2
<211> LENGTH: 658
<212> TYPE: PRT
<213> ORGANISM: Artificial Sequence
<220> FEATURE:
<223> OTHER INFORMATION: Fusion Protein

<400> SEQUENCE: 2

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
                20                  25                  30

Asn Ile Thr Val Thr Leu Lys Lys Phe Pro Leu Asp Thr Leu Ile Pro
            35                  40                  45

Asp Gly Lys Arg Ile Ile Trp Asp Ser Arg Lys Gly Phe Ile Ile Ser
        50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Asn Pro Val Ala Pro
        195                 200                 205

Tyr Trp Thr Ser Pro Glu Lys Met Glu Lys Lys Leu His Ala Val Pro
210                 215                 220

Ala Ala Lys Thr Val Lys Phe Lys Cys Pro Ser Ser Gly Thr Pro Asn
225                 230                 235                 240

Pro Thr Leu Arg Trp Leu Lys Asn Gly Lys Glu Phe Lys Pro Asp His
                245                 250                 255
```

```
Arg Ile Gly Gly Tyr Lys Val Arg Tyr Ala Thr Trp Ser Ile Ile Met
            260                 265                 270

Asp Ser Val Val Pro Ser Asp Lys Gly Asn Tyr Thr Cys Ile Val Glu
            275                 280                 285

Asn Glu Tyr Gly Ser Ile Asn His Thr Tyr Gln Leu Asp Val Val Glu
    290                 295                 300

Arg Ser Pro His Arg Pro Ile Leu Gln Ala Gly Leu Pro Ala Asn Lys
305                 310                 315                 320

Thr Val Ala Leu Gly Ser Asn Val Glu Phe Met Cys Lys Val Tyr Ser
                325                 330                 335

Asp Pro Gln Pro His Ile Gln Trp Leu Lys His Ile Glu Val Asn Gly
            340                 345                 350

Ser Lys Ile Gly Pro Asp Asn Leu Pro Tyr Val Gln Ile Leu Lys Thr
            355                 360                 365

Ala Gly Val Asn Thr Thr Asp Lys Glu Met Glu Val Leu His Leu Arg
            370                 375                 380

Asn Val Ser Phe Glu Asp Ala Gly Glu Tyr Thr Cys Leu Ala Gly Asn
385                 390                 395                 400

Ser Ile Gly Leu Ser His His Ser Ala Trp Leu Thr Val Leu Glu Ala
                405                 410                 415

Leu Glu Glu Arg Pro Ala Val Met Thr Ser Pro Leu Tyr Leu Glu Asp
            420                 425                 430

Lys Thr His Thr Cys Pro Pro Cys Pro Ala Pro Glu Leu Leu Gly Gly
            435                 440                 445

Pro Ser Val Phe Leu Phe Pro Pro Lys Pro Lys Asp Thr Leu Met Ile
            450                 455                 460

Ser Arg Thr Pro Glu Val Thr Cys Val Val Val Asp Val Ser His Glu
465                 470                 475                 480

Asp Pro Glu Val Lys Phe Asn Trp Tyr Val Asp Gly Val Glu Val His
                485                 490                 495

Asn Ala Lys Thr Lys Pro Arg Glu Glu Gln Tyr Asn Ser Thr Tyr Arg
            500                 505                 510

Val Val Ser Val Leu Thr Val Leu His Gln Asp Trp Leu Asn Gly Lys
            515                 520                 525

Glu Tyr Lys Cys Lys Val Ser Asn Lys Ala Leu Pro Ala Pro Ile Glu
    530                 535                 540

Lys Thr Ile Ser Lys Ala Lys Gly Gln Pro Arg Glu Pro Gln Val Tyr
545                 550                 555                 560

Thr Leu Pro Pro Ser Arg Asp Glu Leu Thr Lys Asn Gln Val Ser Leu
                565                 570                 575

Thr Cys Leu Val Lys Gly Phe Tyr Pro Ser Asp Ile Ala Val Glu Trp
            580                 585                 590

Glu Ser Asn Gly Gln Pro Glu Asn Asn Tyr Lys Thr Thr Pro Pro Val
            595                 600                 605

Leu Asp Ser Asp Gly Ser Phe Phe Leu Tyr Ser Lys Leu Thr Val Asp
            610                 615                 620

Lys Ser Arg Trp Gln Gln Gly Asn Val Phe Ser Cys Ser Val Met His
625                 630                 635                 640

Glu Ala Leu His Asn His Tyr Thr Gln Lys Ser Leu Ser Leu Ser Pro
                645                 650                 655

Gly Lys
```

<210> SEQ ID NO 3
<211> LENGTH: 1923
<212> TYPE: DNA
<213> ORGANISM: Artificial Sequence
<220> FEATURE:
<223> OTHER INFORMATION: Polynucleotide encoding fusion protein

<400> SEQUENCE: 3

| | | |
|---|---|---|
| ggtagaccat tcgtagagat gtacagtgaa atccccgaaa ttatacacat gactgaagga | 60 |
| agggagctcg tcattccctg ccgggttacg tcacctaaca tcactgttac tttaaaaaag | 120 |
| tttccacttg acactttgat ccctgatgga aaacgcataa tctgggacag tagaaagggc | 180 |
| ttcatcatat caaatgcaac gtacaaagaa atagggcttc tgacctgtga agcaacagtc | 240 |
| aatgggcatt gtataagac aaactatctc acacatcgac aaaccaatac aatcatagat | 300 |
| gtggttctga gtccgtctca tggaattgaa ctatctgttg gagaaaagct tgtcttaaat | 360 |
| tgtacagcaa gaactgaact aaatgtgggg attgacttca ctgggaata cccttcttcg | 420 |
| aagcatcagc ataagaaact tgtaaaccga gacctaaaaa cccagtctgg gagtgagatg | 480 |
| aagaaatttt tgagcacctt aactatagat ggtgtaaccc ggagtgacca aggattgtac | 540 |
| acctgtgcag catccagtgg gctgatgacc aagaagaaca gcacatttgt cagggtccat | 600 |
| gaaaacccg tagctccata ttggacatcc ccagaaaaga tggaaaagaa attgcatgca | 660 |
| gtgccggctg ccaagacagt gaagttcaaa tgcccttcca gtgggacccc aaaccccaca | 720 |
| ctgcgctggt tgaaaaatgg caaagaattc aaacctgacc acagaattgg aggctacaag | 780 |
| gtccgttatg ccacctggag catcataatg gactctgtgg tgccctctga cagggcaac | 840 |
| tacacctgca ttgtggagaa tgagtacggc agcatcaacc acacatacca gctggatgtc | 900 |
| gtggagcggt cccctcaccg gcccatcctg caagcagggt gcccgccaa caaacagtg | 960 |
| gccctgggta gcaacgtgga gttcatgtgt aaggtgtaca gtgacccgca gccgcacatc | 1020 |
| cagtggctaa agcacatcga ggtgaatggg agcaagattg gccagacaa cctgccttat | 1080 |
| gtccagatct tgaagactgc tggagttaat accaccgaca agagatgga ggtgcttcac | 1140 |
| ttaagaaatg tctcctttga ggacgcaggg gagtatacgt gcttggcggg taactctatc | 1200 |
| ggactctccc atcactctgc atggttgacc gttctggaag ccgacaaaac tcacacatgc | 1260 |
| ccaccgtgcc cagcacctga actcctgggg ggaccgtcag tcttcctctt ccccccaaaa | 1320 |
| cccaaggaca ccctcatgat ctcccggacc cctgaggtca catgcgtggt ggtggacgtg | 1380 |
| agccacgaag accctgaggt caagttcaac tggtacgtgg acggcgtgga ggtgcataat | 1440 |
| gccaagacaa agccgcggga ggagcagtac aacagcacgt accgtgtggt cagcgtcctc | 1500 |
| accgtcctgc accaggactg gctgaatggc aaggagtaca agtgcaaggt ctccaacaaa | 1560 |
| gccctcccag cccccatcga gaaaaccatc tccaaagcca agggcagcc ccgagaacca | 1620 |
| caggtgtaca ccctgccccc atcccgggat gagctgacca gaaccaggt cagcctgacc | 1680 |
| tgcctggtca aaggcttcta tcccagcgac atcgccgtgg agtgggagag caatgggcag | 1740 |
| ccggagaaca actacaagac cacgcctccc gtgctggact ccgacggctc cttcttcctc | 1800 |
| tacagcaagc tcaccgtgga caagagcagg tggcagcagg gaacgtctt ctcatgctcc | 1860 |
| gtgatgcatg aggctctgca caaccactac acgcagaaga gcctctccct gtctccgggt | 1920 |
| aaa | 1923 |

BIFUNCTIONAL ANGIOGENESIS INHIBITOR AND USE THEREOF

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 33518768_1.txt, the date of creation of the ASCII text file is Sep. 16, 2020, and the size of the ASCII text file is 14.0 KB.

FIELD

The present invention relates to a bifunctional angiogenesis inhibitor and the use thereof, in particular to a fusion protein having VEGF inhibitory activity and FGF inhibitory activity as well as its use in inhibiting VEGF and FGF dual factors-induced or high glucose-induced cell proliferation, cell migration, and/or lumen formation, such as inhibiting retinal angiogenesis, angiogenesis-related eye diseases, diabetic retinopathy, age-related macular degeneration and the like.

BACKGROUND

Fundus neovascularization is a serious complication of various eye diseases. Neovascularization can occur in almost all tissues in eyes, such as cornea, iris ciliary body, choroid, retina, macula lutea, and optic disc, causing a series of pathological changes, such as tissue bleeding, exudation and hyperplasia, of these parts, thus damaging the structure and function of the eyeball and seriously damaging the visual function. This series of fundus diseases include diabetic retinopathy (DR), retinopathy of prematurity (ROP), age-related macular degeneration (AMD) and the like, which seriously affect vision and even cause blind.

Studies have shown that VEGF is currently known as the most specific and effective growth factor for angiogenesis. Since the 1990s, drugs targeting VEGF and inhibiting angiogenesis in the fundus by blocking the VEGF signaling pathway have become a hot spot for development. Ranibizumab (trade name Lucentis) can specifically bind to VEGF-A and has been approved by FDA of the United States for the treatment of wet age-related macular degeneration and diabetic macular edema. VEGF Trap-Eye (Aflibercept or Eylea) is an anti-VEGF recombinant protein developed by Regeneron Pharmaceuticals of the United States, and a supplementary application for the treatment of DME has been submitted due to a satisfactory efficacy on DME (diabetic macular edema) demonstrated by the clinical research results. KH902 (Conbercept) is a VEGFR-Fc recombinant protein developed for age-related macular degeneration (AMD) by Chengdu Kanghong Company, which was approved for marketing in December 2013. The successful use of ranibizumab with VEGF as a target in the clinical research and clinical application of DR shows that VEGF is one of the main effective targets of DR.

Although drugs targeting VEGF have made great clinical progress, the regulation of angiogenesis is a very complex process with dynamic balance since angiogenesis is regulated by a variety of factors. Due to great limitations of existing drugs in clinical treatment, how to further improve the clinical treatment effect of anti-angiogenesis drugs is not only a problem needed to be solved by researchers, but also a focus of research and development of the next generation of anti-angiogenesis drugs.

Fibroblast growth factor (FGF), which is a family of growth factors that bind to heparin, plays an important role in various biological functions, such as cell proliferation, differentiation, migration, angiogenesis, and tumorigenesis. It performs its various biological functions by binding to and activating FGF receptors (FGFRs) on the cell surface. Fibroblast growth factor receptor (FGFR) is a receptor that binds to members of the fibroblast growth factor (FGF) family, and part of which is involved in the disease process.

The applicants have disclosed in patent CN201110131029.X a bispecific fusion protein targeting VEGF and FGF ($28^{\#}$ fusion protein in patent CN 201110131029.X, hereinafter referred to as VF28 briefly), the research results showed that VF28 fusion protein had good biological activity and can effectively target VEGF and FGF targets, having a significant effect in the treatment or prevention of tumors and/or ophthalmic angiogenesis diseases. However, it was found during the research that the activity of the prepared VF28 was unstable as the storage time increased. In the long-term tests of 3 batches of VF28 stock solutions (under a long-term test condition of $-80°$ C.$\pm 10°$ C.), binding activity (ELISA method) analysis was performed after placing for 0 hour, 1 month, 3 months, 6 months, and the data showed that there were 1 batch, 2 batches, and 3 batches of VF28 stock solutions, respectively, whose test results of binding activity did not meet the requirements of the evaluation criteria at each monitoring time point of 1 month, 3 months, and 6 months (caused by the non-compliance of the binding activity at the FGF end). In the stability test of the 3 batches of VF28 finished products under an accelerated test condition, cell activity analysis was performed after placing for one month under the accelerated test condition of $25°$ C.$\pm 2°$ C. The results showed that there was one of the three batches of VF28 finished products whose test results of cell activity exceeded the evaluation criteria and did not meet the evaluation criteria.

SUMMARY

In response to the above problems, the present invention provides a structure-modified bifunctional angiogenesis inhibitor RC28-05 targeting VEGF and FGF, which not only has good biological activity and can effectively inhibit retinal angiogenesis, having remarkable therapeutic effect on eye diseases such as diabetic retinopathy, age-related macular degeneration, but also the products prepared thereform are stable in storage, no easy-degradable, and have low requirements on storage temperature and environment.

Specifically, the present invention provides a bifunctional angiogenesis inhibitor having an amino acid sequence shown in SEQ ID NO: 1.

Further, the bifunctional angiogenesis inhibitor has VEGF inhibitory activity and FGF inhibitory activity.

Further, the bifunctional angiogenesis inhibitor can inhibit VEGF and FGF dual factors-induced or high glucose-induced cell proliferation, cell migration, and/or lumen formation.

The present invention provides the use of the above-mentioned bifunctional angiogenesis inhibitor in the manufacture of a medicament for inhibiting retinal angiogenesis.

Further, the use of the above-mentioned bifunctional angiogenesis inhibitor in the manufacture of a medicament for treating angiogenesis-related eye diseases is provided.

Preferably, the angiogenesis-related eye diseases are selected from the group consisting of: age-related macular degeneration such as dry AMD and wet AMD, diabetic retinopathy such as non-proliferative DR, proliferative DR and DME, diabetic macular edema, retinopathy of prematurity and retinal vascular occlusion.

Further, the use of the above-mentioned bifunctional angiogenesis inhibitor in a medicament for improving retinal damage in a subject with diabetes is provided.

Preferably, the retinal damage is short-term retinal damage.

Further, the short-term retinal damage is selected from the group consisting of reducing the number of apoptotic cells in the retinal vascular network, reducing leakage of blood-retinal barrier, inhibiting reactive proliferation of retinal glial cells, and improving ultrastructure of neural retina and retinal blood vessels.

Preferably, the retinal damage is long-term retinal damage.

Further, the long-term retinal damage is selected from the group consisting of improving retinal barrier leakage and inhibiting the thickening of capillary basement membrane.

Further, the use of the above-mentioned bifunctional angiogenesis inhibitor in the manufacture of a medicament for improving the avascular perfusion area of the retina or reducing the number of the nucleus of retinal neovascularization cells in a subject with retinopathy is provided. Preferably, the subject with retinopathy is a premature infant.

Further, the use of the above-mentioned bifunctional angiogenesis inhibitor in the manufacture of a medicament for reducing retinal vascular endothelial cell proliferation, migration and/or lumen formation in a subject is provided.

The present invention also provides an isolated polynucleotide comprising a nucleotide sequence encoding a bifunctional angiogenesis inhibitor, wherein the amino acid sequence of the bifunctional angiogenesis inhibitor is shown in SEQ ID NO: 1 and the nucleotide sequence thereof is shown in SEQ ID NO:3.

The present invention also provides a nucleic acid construct comprising the above polynucleotide, wherein the polynucleotide is operably linked to one or several regulatory sequences that direct the production of the polypeptide in an expression host.

The present invention also provides a vector comprising the above polynucleotide, preferably, the vector is an expression vector, wherein the polynucleotide is operably linked to one or more regulatory sequences that direct the production of the polypeptide in an expression host.

The present invention further provides a host cell comprising the above-mentioned polynucleotide or nucleic acid construct or expression vector, wherein the polynucleotide is operably linked to one or more regulatory sequences that direct the production of the polypeptide. Preferably, the cell is a mammalian cell or a humanized cell. More preferably, the cell is a CHO cell.

The present invention further provides a method for preparing the bifunctional angiogenesis inhibitor, comprising culturing the host cell described in any one of the foregoing items under a condition allowing the expression of the bifunctional angiogenesis inhibitor, and recovering the inhibitor.

The present invention further provides a pharmaceutical composition comprising the polypeptide and/or vector described in any one of the foregoing items.

The present invention further provides a kit comprising the above composition.

DETAILED DESCRIPTION

Figure 1:
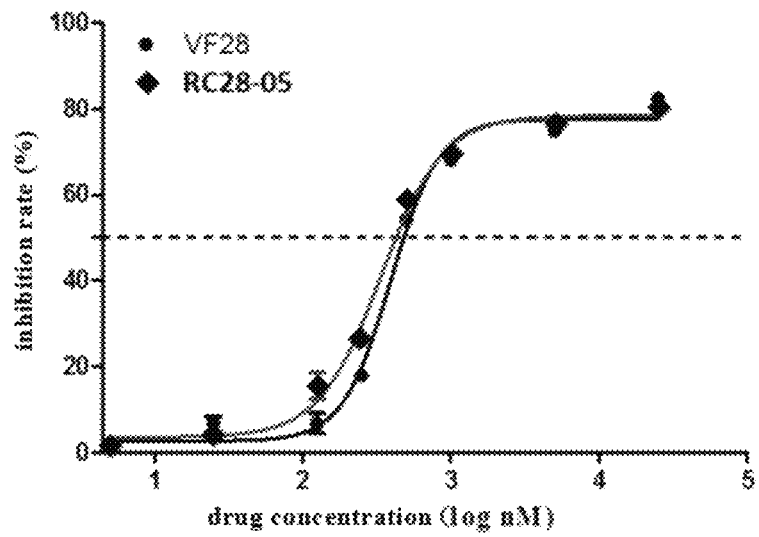
FIG. 1. Inhibitory effects of VF28 and RC28-05 on the proliferation of HUVECs cells stimulated by VEGF165.

Definitions:

Unless otherwise defined, all technical and scientific terms used herein have their ordinary meanings as understood by those of ordinary skill in the art. For definitions and terms in the art, those skilled in the art can specifically refer to *Current Protocols in Molecular Biology* (*Ausubel*). The abbreviations for amino acid residues are the standard 3-letter and/or 1-letter codes used in the art to refer to one of the 20 commonly used L-amino acids.

Although the numerical ranges and parameter approximations shown in the broad scope of the present invention, the numerical values shown in the specific examples are recorded as accurately as possible. However, any numerical value must inherently comprise a certain error, which is caused by the standard deviation in their respective measurements. In addition, all ranges disclosed herein should be understood as covering any and all subranges subsumed therein. For example, a recorded range of "1 to 10" should be considered to include any and all subranges between the minimum value 1 and the maximum value 10 (including the end points); that is, all subranges starting with the minimum value 1 or greater, such as 1 to 6.1, and subranges ending with a maximum value of 10 or less, such as 5.5 to 10. In addition, any reference referred to as "incorporated herein" should be understood as being incorporated in its entirety.

As used herein, the term "soluble" protein refers to a protein that is soluble in an aqueous solution at the biologically relevant temperature, pH level and osmotic pressure. In some specific technical solutions, the fusion protein of the present invention is a soluble fusion protein.

As used herein, the term "isolated" refers to the following substances and/or entities, which are (1) separated from at least some of the components that were originally associated therewith (in the natural environment and/or in a test setting) and/or (2) produced, prepared and/or manufactured artificially. The separated substances and/or entities can be separated from at least about 10%, about 20%, about 30%, about 40%, about 50%, about 60%, about 70%, about 80%, about 90%, about 95%, about 98%, about 99%, substantially 100%, or 100% of other components that were originally associated therewith. In some specific technical solutions, the fusion protein of the present invention is an isolated fusion protein.

The term "VEGF" as used herein refers to the vascular endothelial growth factor. The term "VEGFR" as used herein refers to vascular endothelial growth factor receptor, which can be VEGFR1, VEGFR2, and/or VEGFR3. Preferably, the VEGFR in the present invention is VEGFR1 and/or VEGFR2, preferably human VEGFR.

The term "FGF" as used herein refers to fibroblast growth factor. The term "FGFR" as used herein refers to fibroblast growth factor receptor, which can be FGFR1, FGFR2, FGFR3, and/or FGFR4. Preferably, the FGFR in the present invention is FGFR1, more preferably human FGFR1.

The term "subject" as used herein includes mammals such as humans, such as domestic animals (such as dogs, cats and the like), domestic animals (such as cows, sheep, pigs, horses and the like) or experimental animals (such as monkeys, rats, mice, rabbits, guinea pigs and the like).

The fusion protein of the present invention can further comprise post-translational modifications. Such modifications include but are not limited to acetylation, carboxylation, glycosylation, phosphorylation, lipidation and acylation. As a result, the modified protein can comprise non-amino acid components, such as polyethylene glycol, lipids, polysaccharides or monosaccharides, and phosphoric acid. The effect of such non-amino acid components on protein function can be tested as described herein. When proteins are produced in cells, post-translational processing can also be important for correct folding and/or fusion protein function. Different cells (such as CHO, HeLa, MDCK, 293, WI38, NIH-3T3, or HEK293) have specific cell machinery and unique mechanisms for these post-translational activities, and different cells can be selected to ensure the correct modification and processing of proteins.

The proteins described herein can be produced by any method known in the art. For example, it can be produced by chemical synthesis or from nucleic acid expression. The peptides used in the present invention can be easily prepared according to well-known standard liquid or preferably solid phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984)). The fusion protein can be produced using techniques known in the art to form one or more intramolecular crosslinks between cysteine residues located within the polypeptide sequence expected to be included in the protein (see, for example, U.S. Pat. No. 5,478,925). In addition, the fusion protein described herein can be conventionally modified by adding cysteines or biotins to the C-terminus or N-terminus of the fusion protein.

The term "therapeutically effective amount" or "effective amount" as used herein refers to a dose sufficient to demonstrate its benefit to the subject to be administered. The actual amount, as well as the rate and time course of administration will depend on the subject's own condition and severity. The prescription of treatment (for example, the determination of dosage and the like) is ultimately the responsibility of general practitioners and other doctors and depends on them to make decisions, usually considering the disease to be treated, the individual patient's condition, the delivery site, the method of administration, and other factors known for the doctors.

As used herein, the term "VF28" means a specific VEGFR-FGFR fusion protein, which comprises the second Ig-like domain of VEGFR1, the third Ig-like domain of VEGFR2, and a part derived from the intermediate functional sequence region of the FGFR Ig-like domain, the second Ig-like domain of FGFR, the third Ig-like domain of FGFR and an Fc fragment. VF28 is the abbreviation of 28# fusion protein in Chinese patent 201110131029.X, and the construction process and other information thereof can be found in the disclosure of Chinese patent 201110131029.X. Specifically, the amino acid sequence of VF28 is shown in SEQ ID NO:2.

As used herein, the term "stock solution" refers to a fusion-protein solution that is purified and distributed in an intermediate storage container. The stock solution in the present invention is obtained by affinity chromatography, virus-removal treatment, crude filtration and chromatography as well as precise filtration of the cell culture solution. The term "finished product" as used herein refers to a fusion-protein solution obtained through sterilizing and filtrating the stock solution then packing it in a sterile final container and packaging. The finished product in the present patent is obtained by sterilizing and filtering the stock solution with a certain ratio of auxiliary materials (sodium dihydrogen phosphate, sodium chloride, sucrose, polysorbate 80) added.

As used herein, the term "FGF-Trap" refers to the FGFR-Fc fusion protein, which can be used as a trap for FGF, thereby antagonizing FGF. Specifically, the FGF-Trap used in the examples of the present invention is the 26 #FGFR fusion protein, and the construction process and other information thereof can be found in CN102219860A.

The term "VEGF-Trap" as used herein refers to the VEGFR-Fc fusion protein, which can be used as a trap for VEGF, thereby antagonizing VEGF. Specifically, the VEGF-Trap used in the examples of the present invention is an anti-VEGF recombinant protein (ETLEA, Elia) developed by Regeneron Pharmaceutical Company of the United States, which is commercially available.

The examples are used to further elaborate and explain the present invention, and should not be considered as a limitation of the present invention.

Example 1: Selection of Host Cells

Chinese Hamster Ovary Cells (CHO/dhfr-), which are deficient in dihydrofolate reductase (DHFR) gene, were purchased from ATCC, USA under catalog number CRL-9096 and lot number 3916620. CHO/dhfr-cells were cultured in IMDM complete medium supplemented with hypoxanthine and thymidine (HT) and 10% fetal bovine serum (FBS). The cells were polygonal and growed adherently. After 3 passages, the cells were frozen in liquid nitrogen for storage. In order to obtain CHO/dhfr-cells adapted to serum-free suspension culture, a tube of frozen cells were thawed in a 37° C. water bath, and suspended in Ex-Cell 302 CHO medium (Sigma) containing 10% FBS and HT, then growed adherently in a cell culture flask. When the cells grew well, the cells were suspended in 30 mL of Ex-Cell 302 CHO medium containing 5% fetal bovine serum for shake-flask culture. When the cells grew to $1-2 \times 10^6$/mL, the cells were transferred to Ex-Cell 302 CHO cell culture medium containing 2.5% fetal bovine serum for shake-flask culture. Adaptation was thus achieved step by step in Ex Cell 302 medium containing 1.5% and 0.5% fetal bovine serum, respectively, by shake-flask culture. Finally, the cells were suspended in serum-free Ex Cell 302 CHO medium for shake-flask culture. When the cells grew well, the cells were collected by centrifugation, suspended in Ex-Cell 302 CHO medium containing 10% DMSO, and frozen in liquid nitrogen for storage, which is the original cell bank of CHO cells domesticated by serum-free culture. The CHO cells domesticated by serum-free culture were round or nearly round under suspension culture conditions.

Example 2: Gene of Interest

RC28-05 fusion protein is a fusion protein with bifunctional angiogenesis inhibitory activity, which is composed of partial amino acid sequences of VEGFR and FGFR fused with a human immunoglobulin Fc fragment, the amino acid sequence of which is shown below (as shown in SEQ ID NO:1):

```
GRPFVEMYSE IPEIIHMTEG RELVIPCRVT SPNITVTLKK FPLDTLIPDG KRIIWDSRKG   60
FIISNATYKE IGLLTCEATV NGHLYKTNYL THRQTNTIID VVLSPSHGIE LSVGEKLVLN  120
CTARTELNVG IDFNWEYPSS KHQHKKLVNR DLKTQSGSEM KKFLSTLTID GVTRSDQGLY  180
TCAASSGLMT KKNSTFVRVH EKPVAPYWTS PEKMEKKLHA VPAAKTVKFK CPSSGTPNPT  240
LRWLKNGKEF KPDHRIGGYK VRYATWSIIM DSVVPSDKGN YTCIVENEYG SINHTYQLDV  300
VERSPHRPIL QAGLPANKTV ALGSNVEFMC KVYSDPQPHI QWLKHIEVNG SKIGPDNLPY  360
VQILKTAGVN TTDKEMEVLH LRNVSFEDAG EYTCLAGNSI GLSHHSAWLT VLEADKTHTC  420
PPCPAPELLG GPSVFLFPPK PKDTLMISRT PEVTCVVVDV SHEDPEVKFN WYVDGVEVHN  480
AKTKPREEQY NSTYRVVSVL TVLHQDWLNG KEYKCKVSNK ALPAPIEKTI SKAKGQPREP  540
QVYTLPPSRD ELTKNQVSLT CLVKGFYPSD IAVEWESNGQ PENNYKTTPP VLDSDGSFFL  600
YSKLTVDKSR WQQGNVFSCS VMHEALHNHY TQKSLSLSPG K                     641
```

The nucleotide sequence of RC28-05 is shown below [20] (1923 bp) (as shown in SEQ ID NO: 3):

```
ggtagaccat tcgtagagat gtacagtgaa atccccgaaa ttatacacat gactgaagga    60
agggagctcg tcattccctg ccgggttacg tcacctaaca tcactgttac tttaaaaaag  120
tttccacttg acactttgat ccctgatgga aaacgcataa tctgggacag tagaaagggc  180
ttcatcatat caaatgcaac gtacaaagaa atagggcttc tgacctgtga agcaacagtc  240
aatgggcatt tgtataagac aaactatctc acacatcgac aaaccaatac aatcatagat  300
gtggttctga gtccgtctca tggaattgaa ctatctgttg gagaaaagct tgtcttaaat  360
tgtacagcaa gaactgaact aaatgtgggg attgacttca actgggaata cccttcttcg  420
aagcatcagc ataagaaact tgtaaaccga gacctaaaaa cccagtctgg gagtgagatg  480
aagaaatttt tgagcacctt aactatagat ggtgtaaccc ggagtgacca aggattgtac  540
acctgtgcag catccagtgg gctgatgacc aagaagaaca gcacatttgt cagggtccat  600
gaaaaacccg tagctccata ttggacatcc ccagaaaaga tggaaaagaa attgcatgca  660
gtgccggctg ccaagacagt gaagttcaaa tgcccttcca gtgggacccc aaaccccaca  720
ctgcgctggt tgaaaaatgg caaagaattc aaacctgacc acagaattgg aggctacaag  780
gtccgttatg ccacctggag catcataatg gactctgtgg tgccctctga caagggcaac  840
tacacctgca ttgtggagaa tgagtacggc agcatcaacc acacatacca gctggatgtc  900
gtggagcggt cccctcaccg gcccatcctg aagcagggt tgcccgccaa caaaacagtg  960
gccctgggta gcaacgtgga gttcatgtgt aaggtgtaca gtgacccgca gccgcacatc 1020
cagtggctaa agcacatcga ggtgaatggg agcaagattg gcccagacaa cctgccttat 1080
gtccagatct tgaagactgc tggagttaat accaccgaca agagatgga ggtgcttcac 1140
ttaagaaatg tctcctttga ggacgcaggg gagtatacgt gcttggcggg taactctatc 1200
ggactctccc atcactctgc atggttgacc gttctggaag ccgacaaaac tcacacatgc 1260
ccaccgtgcc cagcacctga actcctgggg ggaccgtcag tcttcctctt ccccccaaaa 1320
cccaaggaca ccctcatgat ctcccggacc cctgaggtca catgcgtggt ggtggacgtg 1380
agccacgaag accctgaggt caagttcaac tggtacgtgg acggcgtgga ggtgcataat 1440
gccaagacaa agccgcggga ggagcagtac aacagcacgt accgtgtggt cagcgtcctc 1500
```

-continued

```
accgtcctgc accaggactg gctgaatggc aaggagtaca agtgcaaggt ctccaacaaa  1560
gccctcccag cccccatcga gaaaaccatc tccaaagcca aagggcagcc ccgagaacca  1620
caggtgtaca ccctgccccc atcccgggat gagctgacca agaaccaggt cagcctgacc  1680
tgcctggtca aaggcttcta tcccagcgac atcgccgtgg agtgggagag caatgggcag  1740
ccggagaaca actacaagac cacgcctccc gtgctggact ccgacggctc cttcttcctc  1800
tacagcaagc tcaccgtgga caagagcagg tggcagcagg ggaacgtctt ctcatgctcc  1860
gtgatgcatg aggctctgca caaccactac acgcagaaga gcctctccct gtctccgggt  1920
aaa                                                                 1923
```

A conventional expression vector were inserted after introducing double cleavage sites at both ends of the RC28-05 target gene sequence. CHO cells were transfected by a general method to select an RC28-05 expressing cell strain, and expression of the RC28-05 fusion protein was performed.

Example 3: Affinity Test of the Fusion Protein

VF28 and RC28-05 were tested for the affinity using ForteBio Octet (PALL). PBS (pH 7.4) was added as a balanced solution to each well of column 1 of the detection plate A-E, and the probe was soaked and activated for 10 min; RC28-05 and VF28 were diluted respectively to a concentration of 50 nM with PBS and added to column 2 of rows A-E of the 96-well assay plate with the program set to Loading for 300 s; PBS was added as a balanced solution to each well of column 3 of rows A-E of the detection plate with the program set to Baseline for 180 s; rhVEGF (R&D) and rhFGF (R&D) were diluted respectively to a concentration of 500 nM and 400 nM using PBS as the diluent, and then serially diluted at 1:2 for three gradients (a total of four gradients) to a concentration of 62.5 nM and 50 nM. The serially diluted samples were added to column 4 of rows A-D of the 96-well plate while the dilution was added to column 4 of row E as a negative control, with the program set to Association for 600 s; PBS was added as the dissociation solution to each well in column 5 of rows A-E with the program set to Dissociation for 1800 s; 10 mM glycine (pH 1.5) and PBS were added as the regeneration solution and the neutralization solution in columns 6 and 7 of rows A-E, respectively, with the programs respectively set to Regeneration and Neutralization for 15 s each, repeating for 5 times. A total of 3 cycles were tested. Data was analysed using Data analysis 7.0 software. The equilibrium constant (KD) value was calculated with the background subtracted using the corresponding unbound rhVEGF/rhFGF sensor as a control. The results were shown in Table 1. The results showed that RC28-05 and VF28 had good affinity with rhVEGF and rhFGF.

Example 4: Cell Activity Experiment of Fusion Protein

Figure 2:
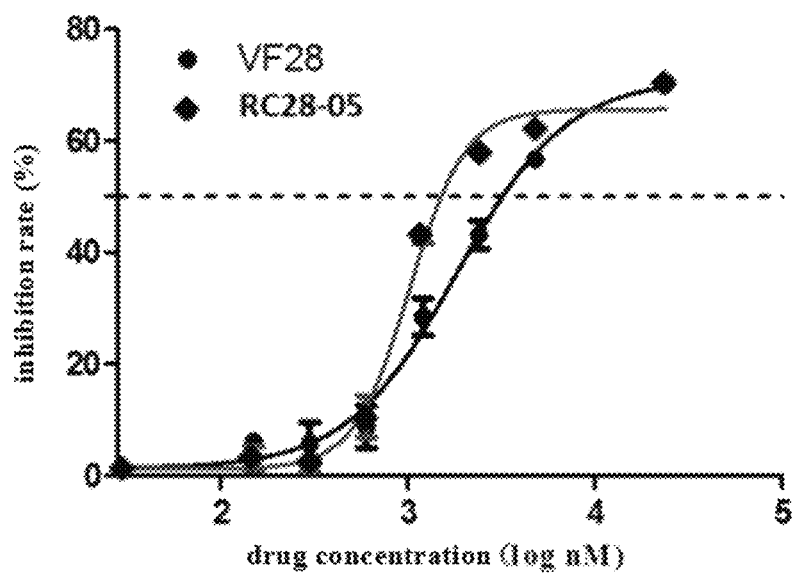
FIG. 2. Inhibitory effects of VF28 and RC28-05 on the proliferation of HUVECs cells stimulated by bFGF.

HUVEC cells within 10 passages were inoculated to a 96-well plate at 100 μL/well (i.e. 5000 cells/well) with the density adjusted to $5×10^4$ cells/mL. After the cells adhered, conditioned medium or VEGF165 or bFGF factor (40 ng/mL) or VEGF165+different concentrations of RC28-05 or VF28 drugs (final concentrations of 0, 0.0125, 0.0625, 0.125, 0.25, 0.5, 1, 5, 25 nM) or bFGF+different concentrations of RC28-05 or VF28 drugs (final concentrations of 0, 0.0156, 0.0625, 0.25, 0.5, 1, 2, 8, 32 nM) were added at 100 μL/well with a final culture volume of 200 μL/well, 3 replicate wells per sample; culture was continuously performed at 37° C. in a 5% CO2 incubator. 72 hours after drug addition, the culture medium in the 96-well plate was spin-dried, and the endothelial cell basic culture medium containing 10% CCK-8 was added to each well at 100 μL/well. Incubation was performed at 37° C. for 4 hours, and OD450 was detected using a microplate reader. The inhibition rate of the corresponding drugs on the proliferation of HUVEC cells promoted by VEGF165/bFGF at each concentration was calculated as inhibition rate of cell proliferation %=(OD factor−OD(factor+drug))/OD factor×100. The $IC_{50}$ values of the drugs were calculated by Prism software, and the inhibition rates of the maximum drug concentration were tested adopting measured values. The differences between RC28-05 and VF28 in inhibiting HUVEC cell proliferation under stimulation of VEGF165/bFGF were compared. The inhibition results of VF28 and RC28-05 on the proliferation of HUVEC cells stimulated by VEGF165/bFGF were shown in FIG. 1 and FIG. 2, and the maximum inhibition rate and IC50 values statistics were shown in Table 2. The results showed that RC28-05 and VF28 had significant inhibitory effects on the proliferation of HUVEC cells stimulated by VEGF165/bFGF.

TABLE 1

Statistics of affinity comparison results of RC28-05 and VF28

| Samples | Factors | Equilibrium Constant KD (M) | Binding Constant kon(1/Ms) | Dissociation Constant kdis(1/s) | N |
| --- | --- | --- | --- | --- | --- |
| RC28-05 | rhVEGF165 | 2.70E−10 ± 1.28E−10 | 2.30E+05 ± 0.64E+05 | 5.65E−05 ± 0.75E−05 | 3 |
| VF28 | rhVEGF165 | 2.51E−10 ± 5.65E−11 | 2.76E+05 ± 7.94E+04 | 6.68E−05 ± 1.31E−05 | 3 |
| RC28-05 | rhFGF2 | 3.28E−09 ± 1.60E−09 | 2.66E+04 ± 1.01E+04 | 7.96E−05 ± 2.42E−05 | 3 |
| VF28 | rhFGF2 | 5.24E−09 ± 2.07E−09 | 1.90E+04 ± 1.74E+03 | 9.78E−05 ± 3.26E−05 | 3 |

TABLE 2

Inhibitory effects of RC28-05 and VF28 on the proliferation of HUVEC cells stimulated by VEGF165/bFGF

| Drugs | Stimulating Factors | $IC_{50}$(nM) | Maximum Inhibition Rate (%) |
|---|---|---|---|
| VF28 | $VEGF_{165}$ | 0.48 | 82.34 ± 1.83 |
|  | bFGF | 3.20 | 70.16 ± 2.79 |
| RC28-05 | $VEGF_{165}$ | 0.43 | 80.19 ± 0.27 |
|  | bFGF | 1.50 | 70.40 ± 1.05 |

Example 5: Preparation of RC28-05 Stock Solutions and Finished Products

The preparation method of RC28-05 stock solutions and finished products was the same as that of VF28, which specifically was:

1) After centrifuging the cell culture solution, the supernatant was collected for protein A affinity chromatography;

2) After all the collected eluate was treated with organic solvents/detergents (S/D), 1% polysorbate 80 (W/V) and 0.3% tributyl phosphate (W/V) were added to the eluate and placed at 20-25° C. for 6h to inactivate lipid-enveloped viruses;

3) After the above treatment, Sepharose cation exchange chromatography was used to remove related impurities such as polymers and degradation products;

4) Anion exchange chromatography was performed on all the collected eluates to remove a small amount of aggregates, CHO host cell proteins, host DNA and endotoxins and the like;

5) The penetrating fluid after the above chromatography was collected and then nano-membrane filtrated to remove non-lipid enveloped viruses;

6) After ultrafiltration and concentration of the protein solution after the nano-membrane filtration to a certain concentration (10-15 mg/mL), a buffer solution of 10-12 times the volume of the concentrated protein (0.02 mol/L sodium dihydrogen phosphate, 0.015 mol/L sodium chloride, 0.2 mol/L sucrose, PH 6.8) was used for substitution dialysis, then the protein solution was concentrated (40-45 mg/mL). After 0.02% (W/V) polysorbate 80 was added and stirred to dissolve, filtration was performed using 0.45+0.2 μm membrane, and the resultant protein solution was RC28-05 stock solutions with a protein concentration of 40-45 mg/mL.

7) Preparation of finished products: The preparation method of 1000 tubes of finished products of 40 mg/mL (0.2 ml/tube) was as follows. The concentration of RC28-05 protein in the above protein stock solutions was determined and defined as C mg/mL, and a total of 220 ml of protein solution needed to be prepared considering 10% of the filling loss. Then the total amount of protein required was 220 ml*40 mg/mL*0.2 ml=8.8 g protein, and the protein stock solution volume required was V=8.8/C*1000 (mL). A buffer solution (0.02 mol/L sodium dihydrogen phosphate, 0.015 mol/L sodium chloride, 0.2 mol/L sucrose, 0.02% (W/V) polysorbate 80) was added to a V mL protein stock solution till a volume of 220 mL and mixed homogeneously. Filteration was performed using a filter membrane with a pore size of not more than 0.22 μm for sterilization. RC28-05 finished products were obtained after packaging, rolling aluminum cover and boxing.

Example 6: Stability Test of RC28-05 (Stock Solutions/Finished Products)

1. Stability Test of RC28-05 Stock Solutions (1) Purity Analysis of Different Storage Time (−80° C.±10° C.)

① SEC-HPLC Method 3 batches of RC28-05 stock solutions (batch numbers: RC28-05-YY20160329, RC28-05-YY20160330, RC28-05-YY20160331) were placed under a long-term test condition of −80° C.±10° C. for 0 hours, 6 months, 9 months and 12 months for purity analysis (SEC-HPLC method). The test results of the SEC purity of the test samples at each monitoring time point showed that the main peaks were all ≥95.0%. See Table 14 for details.

TABLE 14

Test results of the SEC purity of RC28-05 stock solutions (−80° C. ± 10° C.) (%)

| Batches | Periods SEC purity % | | | |
|---|---|---|---|---|
|  | T0 | 6 m | 9 m | 12 m |
| RC28-05-YY20160329 | 98.4 | 98.2 | 98.5 | 100.0 |
| RC28-05-YY20160330 | 98.0 | 97.9 | 98.1 | 99.8 |
| RC28-05-YY20160331 | 97.7 | 97.5 | 97.8 | 99.2 |

Note:
The evaluation criterion for the SEC purity was the main peak ≥95.0%;
"m" stands for "month".

② SDS-PAGE Method 3 batches of RC28-05 stock solutions (batch numbers: RC28-05-YY20160329, RC28-05-YY20160330, RC28-05-YY20160331) were placed under a long-term test condition of −80° C.±10° C. for 0 hours, 6 months, 9 months and 12 months for purity analysis (SDS-PAGE method). The results were shown in Table 15. The data showed that as the storage time increased, the test results of the SDS-PAGE reducing purity of RC28-05 stock solutions were all higher than 90%.

TABLE 15

Test results of the SDS-PAGE purity of RC28-05 stock solutions (−80° C. ± 10° C.) (%)

| Batches | Period SDS-PAGE reducing purity % | | | |
|---|---|---|---|---|
|  | T0 | 6 m | 9 m | 12 m |
| RC28-05-YY20160329 | 98.1 | 98.3 | 97.7 | 97.6 |
| RC28-05-YY20160330 | 98.1 | 98.1 | 97.8 | 97.5 |
| RC28-05-YY20160331 | 98.8 | 98.2 | 97.1 | 97.8 |

Note:
The evaluationcriterion for the SDS-PAGE purity was non-reducing purity ≥90%;
"m" stands for "month".

(2) Cell Activity Experiment of Stock Solutions at Different Storage Time (−80° C.±10° C.)

3 batches of RC28-05 stock solutions (batch numbers: RC28-05-YY20160329, RC28-05-YY20160330, RC28-05-YY20160331) were placed under a long-term test condition of −80° C.±10° C. for 12 months for cell activity analysis; the results showed that it was found through cell activity analysis of RC28-05 stock solutions placed at −80° C.±10° C. for 12 months that the relative activity of the cells at each monitoring time point in the test period all met the quality requirements. See Table 16 for details.

TABLE 16

Test results of the relative cell activity of RC28-05 stock solutions (−80° C. ± 10° C.) (%)

| Batches | Periods Relative Cell activity % | | | |
|---|---|---|---|---|
| | T0 | 6 m | 9 m | 12 m |
| RC28-05-YY20160329 | 85.1 | 92.8 | 81.8 | 103.3 |
| RC28-05-YY20160330 | 93.0 | 88.1 | 77.7 | 95.7 |
| RC28-05-YY20160331 | 86.7 | 100.5 | 92.7 | 106.0 |

Note:
The evaluation criterion for the relative cell activity was that the relative cell activity should be 70% to 130%;
"m" stands for "month".

(3) Binding Activity Experiment of Stock Solutions at Different Storage Time (−80° C.±10° C.)

3 batches of RC28-05 stock solutions (batch numbers: RC28-05-YY20160329, RC28-05-YY20160330, RC28-05-YY20160331) were placed under a long-term test condition of −80° C.±10° C. for 12 months for binding activity analysis (ELISA method); the results showed that it was found through the relative binding activity test analysis of RC28-05 stock solutions placed at −80° C.±10° C. for 12 months that the relative activity of the cells at each monitoring time point in the test period all met the quality requirements. See Table 17 for details.

TABLE 17

Test results of the relative binding activity of RC28-05 stock solutions (−80° C. ± 10° C.) (%)

| Batches | Periods Relative binding activity | | | | |
|---|---|---|---|---|---|
| | T0 | | 6 m | 9 m | 12 m |
| | VEGF | FGF | | | |
| RC28-05-YY20160329 | 87.6 | 97.4 | 101.4 | 114.6 | 92.9 |
| RC28-05-YY20160330 | 120.2 | 109.6 | 99.6 | 105.0 | 105.6 |
| RC28-05-YY20160331 | 103.0 | 94.5 | 101.5 | 103.6 | 118.9 |

Note:
The evaluation criterion for the relative binding activity was that the relative binding activity should be 70% to 130%;
T0 was of the dual system analysis, while the remaining time points were of the single system analysis;
"m" stands for "month".

2. RC28-05 Finished Product Stability Test (1) Purity Analysis at Different Storage Time ① SEC-HPLC Method 3 batches of RC28-05 finished products (batch numbers: RC28-05-20160401-1, RC28-05-20160401-2, RC28-05-20160401-3) were placed under a long-term test condition of 5° C.±3° C. for 12 months, under an accelerated test condition of 25° C.±2° C. for 1 month, respectively, for purity analysis (SEC-HPLC method). The experimental results showed that it was found through purity analysis (SEC-HPLC method) of the finished product placed under a long-term test condition of 5° C.±3° C. for 12 months that the test results of the SEC purity of the test samples at each monitoring time point during the experimental period were all about 95%; whereas when the finished product was placed under an accelerated test condition of 25° C.±2° C. for 1 month, the test results of the SEC purity of the test samples at each monitoring time point showed that the main peak were all ≥95.0%. See Table 18 and Table 19 for details.

TABLE 18

Test results of the SEC purity of RC28-05 finished products (5° C. ± 3° C.) (%)

| Batches | Periods SEC purity | | | | |
|---|---|---|---|---|---|
| | T0 | 3 m | 6 m | 9 m | 12 m |
| RC28-05-20160401-1 | 98.4 | 98.4 | 97.4 | 96.9 | 97.9 |
| RC28-05-20160401-2 | 98.1 | 98.1 | 97.0 | 96.6 | 97.1 |
| RC28-05-20160401-3 | 97.7 | 97.7 | 96.7 | 96.4 | 96.9 |

Note:
The evaluation criterion for the SEC purity was the main peak ≥95.0%;
"m" standed for "month".

TABLE 19

Test results of the SEC purity of RC28-05 finished products (25° C. ±2° C.) (%)

| Batches | Periods SEC purity | | | |
|---|---|---|---|---|
| | 0 d | 10 d | 20 d | 30 d |
| RC28-05-20160401-1 | 98.4 | 96.6 | 96.1 | 96.6 |
| RC28-05-20160401-2 | 98.1 | 96.3 | 95.8 | 96.1 |
| RC28-05-20160401-3 | 97.7 | 96.2 | 95.6 | 95.9 |

Note:
The evaluation criterion for the SEC purity was the main peak ≥95.0%;
"m" stands for "month".

② SDS-PAGE Method 3 batches of RC28-05 finished products (batch numbers: RC28-05-20160401-1, RC28-05-20160401-2, RC28-05-20160401-3) were placed under a long-term test condition of 5° C.±3° C. for 12 month, at 25° C.±2° C. for 1 month, respectively, for purity analysis (SDS-PAGE method). The results showed that it was found through purity analysis (SDS-PAGE) of the RC28-05 finished product placed at 5° C.±3° C. for 12 months that the test results of SDC-PAGE reducing purity of the test samples at each monitoring time point in the test period were all greater than 90.0%; through purity (SDS-PAGE) analysis of the RC28-05 finished product placed at 25° C.±2° C. for 6 months, it was found that the reducing purity of SDC-PAGE of the tested samples at each monitoring time point had a downward trend, while the test results were all greater than 90.0%. See Table 20 and Table 21 for details.

TABLE 20

Test results of the SDS-PAGE purity of RC28-05 finished products (5° C. ± 3° C.) (%)

| Batches | Periods SDS-PAGE reduction | | | | |
|---|---|---|---|---|---|
| | 0 h | 3 m | 6 m | 9 m | 12 m |
| RC28-05-20160401-1 | 98.9 | 97.7 | 97.0 | 96.9 | 95.7 |
| RC28-05-20160401-2 | 97.9 | 97.6 | 96.7 | 97.7 | 95.9 |
| RC28-05-20160401-3 | 98.0 | 97.6 | 97.0 | 96.9 | 96.3 |

Note:
The evaluation criterion for the SDS-PAGE purity was non-reducing purity ≥90%;
"m" stands for "month".

TABLE 21

Test results of the SDS-PAGE reducing purity of RC28-05 finished products (25° C. ± 2° C.) (%)

| Batches | Periods SDS-PAGE reduction | | | |
|---|---|---|---|---|
| | 0 h | 10 d | 20 d | 30 d |
| RC28-05-20160401-1 | 98.9 | 96.3 | 97.5 | 97.8 |
| RC28-05-20160401-2 | 97.9 | 96.1 | 97.4 | 97.6 |
| RC28-05-20160401-3 | 98.0 | 96.0 | 96.8 | 98.1 |

Note:
The evaluationcriterion for the SDS-PAGE purity was non-reducing purity ≥90%;
"d" stands for "day".

(2) Cell Activity Experiment of Finished Products at Different Storage Time 3 batches of finished products of RC28-05 (batch numbers: RC28-05-20160401-1, RC28-05-20160401-2, RC28-05-20160401-3) were placed under a long-term test condition of 5° C.±3° C. for 12 months, at 25° C.±2° C. for 1 month, respectively, for cell activity analysis. The results showed that it was found through cell activity analysis of the finished product placed at 5° C.±3° C. for 12 months that the relative cell activity results of the test samples at each monitoring time point during the test period all met the requirements of the evaluation criteria; the test results of the relative cell activity at each monitoring time point during the test period all met the quality requirements through cell activity analysis of the finished product placed at 25° C.±2° C. for 1 month. See Table 22 and Table 23 for details.

TABLE 22

Test results of the relative cell activity of RC28-05 finished products (5° C. ± 3° C.) (%)

| Batches | Periods Relative cell activity | | | | |
|---|---|---|---|---|---|
| | 0 h | 3 m | 6 m | 9 m | 12 m |
| RC28-05-20160401-1 | 120.8 | 125.1 | 111.8 | 85.4 | 100.2 |
| RC28-05-20160401-2 | 104.3 | 125.1 | 96.1 | 85.0 | 103.4 |
| RC28-05-20160401-3 | 105.2 | 111.7 | 100.5 | 93.7 | 100.3 |

Note:
The evaluation criterion for the relative cell activity was that the relative cell activity should be 70% to 130%;
"m" stands for "month".

TABLE 23

Test results of the relative cell activity of RC28-05 finished products (25° C. ± 2° C.) (%)

| Batches | Periods Relative cell activity | | | |
|---|---|---|---|---|
| | 0 h | 10 d | 20 d | 30 d |
| RC28-05-20160401-1 | 120.8 | 103.4 | 88.7 | 110.0 |
| RC28-05-20160401-2 | 104.3 | 93.4 | 90.6 | 108.4 |
| RC28-05-20160401-3 | 105.2 | 94.4 | 88.0 | 104.1 |

Note:
The evaluation criterion for the relative cell activity was that the relative cell activity should be 70% to 130%;
"d" stands for "day".

(3) Binding Activity Experiment of Finished Products at Different Storage Time 3 batches of RC28-05 finished products (batch numbers: RC28-05-20160401-1, RC28-05-20160401-2, RC28-05-20160401-3) were placed under a long-term test condition of 5° C.±3° C. for 12 months, at 25° C.±2° C. for 1 month, respectively, for binding activity analysis. The results showed that it was found through the binding activity analysis of the finished products placed at 5° C.±3° C. for 12 months that the results of the relative binding activity of the test samples at each monitoring time point during the test period all met the requirements of the evaluation criteria; through the binding activity analysis of the finished products at 25° C.±2° C. for 1 month, the relative binding activity (the VEGF end and the FGF end) test results at each monitoring time point in the test period all met the quality requirements. See Table 24 and Table 25 for details.

TABLE 24

Test results of the relative binding activity of RC28-05 finished products (5° C. ± 3° C.) (%)

| Batches | Periods Relative binding activity | | | | |
|---|---|---|---|---|---|
| | 0 h (VEGF; FGF) | 3 m | 6 m | 9 m | 12 m |
| RC28-05-20160401-1 | 72.8; 90.5 | 111.6 | 107.6 | 104.9 | 119.3 |
| RC28-05-20160401-2 | 76.9; 76.5 | 116.1 | 102.4 | 112.0 | 109.8 |
| RC28-05-20160401-3 | 85.5; 86.1 | 107.1 | 98.5 | 110.2 | 111.1 |

Note:
The evaluation criterion for the relative binding activity was that the relative binding activity should be 70% to 130%;
0 h was of the dual system analysis, while the remaining time points were of the single system analysis;
"m" stands for "month".

TABLE 25

Test results of the relative binding activity of RC28-05 finished products (25° C. ± 2° C.) (%)

| Batches | Periods Relative binding activity | | | |
|---|---|---|---|---|
| | 0 h (VEGF; FGF) | 10 d | 20 d | 30 d |
| RC28-05-20160401-1 | 72.8; 90.5 | 112.4 | 104.5 | 95.7 |
| RC28-05-20160401-2 | 76.9; 76.5 | 109.4 | 120.5 | 101.2 |
| RC28-05-20160401-3 | 85.5; 86.1 | 107.8 | 118.6 | 113.1 |

Note:
The evaluation criterion for the relative binding activity was that the relative binding activity should be 70% to 130%;
0 h was of the dual system analysis, while the remaining time points were of the single system analysis;
"d" stands for "day".

3. Experimental Conclusions

The storage of 3 batches of RC28-05 stock solutions (batch numbers: RC28-05-YY20160329, RC28-05-YY20160330, RC28-05-YY20160331) under a long-term test condition of −80° C.±10° C. was investigated. The results were:

① SEC purity: 3 batches of RC28-05 stock solutions were placed at a condition of −80° C.±10° C. for 12 months with their SEC purity all ≥90%.

② SDS-PAGE reducing purity: 3 batches of RC28-05 stock solutions were placed at −80° C.±10° C. for 12 months with their reducing purity was all ≥90%.

③ Cell activity: 3 batches of RC28-05 stock solutions were placed at −80° C.±10° C. for 12 months. It was found through the cell activity analysis that relative activity of the cells at each monitoring time point in the test period all met the quality requirements.

④ Binding activity: 3 batches of RC28-05 stock solutions were placed at −80° C.±10° C. for 12 months. It was found through the cell activity analysis that relative activity of the cells at each monitoring time point in the test period all met the quality requirements.

The storage of 3 batches of RC28-05 finished products (batch numbers: RC28-05-20160401-1, RC28-05-20160401-2, RC28-05-20160401-3) under a condition of 5° C.±3° C., 25° C.±2° C., respectively, was investigated. The results were:

① Sec Purity:

3 batches of RC28-05 finished products were placed at a condition of 5° C.±3° C. for 12 months with their SEC purity all ≥90%;

3 batches of RC28-05 finished products were placed at a condition of 25° C.±2° C. for 1 month with their SEC purity all ≥90%.

② SDS-PAGE Reducing Purity:

3 batches of RC28-05 finished products of RC28-05 were placed at a condition of 5° C.±3° C. for 12 months with their SDS-PAGE reducing purity all ≥90%;

3 batches of RC28-05 finished products of RC28-05 were placed at a condition of 25° C.±2° C. for 1 months with their SDS-PAGE reducing purity all ≥90%.

③ Cell Activity:

3 batches of RC28-05 finished products were placed at a condition of 5° C.±3° C. for 12 months, and the test results of cell activity of the test samples at each monitoring time point all met the requirements of the evaluation criteria;

3 batches of RC28-05 finished products were placed at a condition of 25° C.±2° C. for 1 month, and the test results of cell activity of the test samples at each monitoring time point all met the requirements of the evaluation criteria.

④ Binding Activity:

3 batches of RC28-05 finished products were placed at 5° C.±3° C. for 12 months, and the test results of cell activity of the test samples at each monitoring time point all met the requirements of the evaluation criteria;

3 batches of RC28-05 finished products were placed at 25° C.±2° C. for 1 month, and the test results of cell activity of the test samples at each monitoring time point all met the requirements of the evaluation criteria.

From this, the following conclusions can be drawn:

① RC28-05 stock solutions can be stored stably for at least 12 months under the condition of −80° C.±10° C., whereas VF28 stock solutions did not meet the activity requirements after 6 months under the same condition.

② RC28-05 finished products can be stored stably for at least 12 months under the condition of 5° C.±3° C., whereas VF28 was stored stably under the same condition for 6 months.

③ RC28-05 finished products can be stored stably at 25° C.±2° C. for at least 1 month, whereas ⅓ of the batches of VF28 stock solution did not meet the activity requirements under the same condition.

In summary, RC28-05 stock solutions were stable at −80° C.±10° C., while RC28-05 finished products were stored stably under the condition of 5° C.±3° C. (for at least 12 months) and 25° C.±2° C. (for at least 1 month), the stable storage time of which was much longer than VF28 under the same condition.

The present invention has been exemplified by various specific examples. However, a person of ordinary skill in the art can understand that the present invention is not limited to each specific embodiments, and a person of ordinary skill can make various changes or modifications within the scope of the present invention, and each technical feature mentioned in various places in this specification can be combined with each other without departing from the spirit and scope of the present invention. Such changes and modifications are within the scope of the present invention.

The invention claimed is:

1. A bifunctional angiogenesis inhibitor having the amino acid sequence shown in SEQ ID NO: 1.

2. A pharmaceutical composition comprising the polypeptide as claimed in claim 1.

3. A kit comprising the pharmaceutical composition of claim 2.

4. A method of inhibiting VEGF and FGF dual factor-induced cell proliferation, cell migration, and/or lumen formation comprising administering the bifunctional angiogenesis inhibitor of claim 1 to a subject in need thereof.

5. A method of inhibiting retinal angiogenesis comprising administering the bifunctional angiogenesis inhibitor of claim 1 to a subject in need thereof.

6. A method of treating angiogenesis-related eye diseases comprising administering the bifunctional angiogenesis inhibitor of claim 1 to a subject in need thereof.

7. The method according to claim 6, wherein the angiogenesis-related eye diseases are selected from the group consisting of: age-related macular degeneration, diabetic retinopathy (DR), proliferative DR, diabetic macular edema, retinopathy of prematurity and retinal vascular occlusion.

8. A method of improving retinal damage in a subject with diabetes comprising administering the bifunctional angiogenesis inhibitor of claim 1 to the subject.

9. The method according to claim 8, wherein the retinal damage is short-term retinal damage or long-term retinal damage.

10. The method according to claim 9, wherein the improvement to the short-term retinal damage is selected from the group consisting of reducing the number of apoptotic cells in the retinal vascular network, reducing leakage of the blood-retinal barrier, inhibiting reactive proliferation of retinal glial cells, and improving ultrastructure of neural retina and retinal blood vessels; and the improvement to the long-term retinal damage is selected from the group consisting of improving retinal barrier leakage and inhibiting the thickening of capillary basement membrane.

11. A method of improving the avascular perfusion area of the retina or reducing the number of nuclei of retinal neovascularization cells in a subject with retinopathy comprising administering the bifunctional angiogenesis inhibitor of claim 1 to the subject.

12. The method according to claim 11, wherein the subject with retinopathy is a premature infant.

13. An isolated polynucleotide comprising a nucleotide sequence encoding a bifunctional angiogenesis inhibitor, wherein the amino acid sequence of the bifunctional angiogenesis inhibitor is shown in SEQ ID NO: 1.

14. The polynucleotide of claim 13 having the nucleotide sequence shown in SEQ ID NO:3.

15. A nucleic acid construct comprising the polynucleotide of claim 13, wherein the polynucleotide is operably linked to one or more regulatory sequences directing the production of the polypeptide in an expression host.

16. A vector comprising the polynucleotide of claim 13, wherein the polynucleotide is operably linked to one or more regulatory sequences.

17. The vector of claim 16, wherein the vector is an expression vector, and the regulatory sequence directs the production of the polypeptide in an expression host.

18. A host cell comprising the polynucleotide of claim 13, wherein the polynucleotide is operably linked to one or more regulatory sequences directing the production of the polypeptide.

19. The host cell of claim 18, which is a mammalian cell or a humanized cell.

20. A method for preparing a bifunctional angiogenesis inhibitor having the amino acid sequence shown in SEQ ID NO:1 comprising culturing the host cell as claimed in claim 18 under a condition allowing the expression of the bifunctional angiogenesis inhibitor and recovering the inhibitor.

21. The host cell of claim 18, wherein the mammalian cell is a Chinese Hamster Ovary (CHO) cell.

* * * * *